US006815565B2

(12) United States Patent
Mills et al.

(10) Patent No.: US 6,815,565 B2
(45) Date of Patent: Nov. 9, 2004

(54) METHOD FOR PREPARING HYDROQUINONES AND DIHYDROXYBIPHENYL COMPOUNDS FROM MIXTURES OF BROMOPHENOLS AND BENZOQUINONES

(75) Inventors: Ryan Christopher Mills, Mechanicville, NY (US); Eric James Pressman, East Greenbush, NY (US); Timothy Leigh Chuck, Canajoharie, NY (US); John Yaw Ofori, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 10/704,002

(22) Filed: Nov. 7, 2003

(65) Prior Publication Data

US 2004/0199027 A1 Oct. 7, 2004

Related U.S. Application Data

(63) Continuation-in-part of application No. 10/406,061, filed on Apr. 4, 2003, now Pat. No. 6,693,221.

(51) Int. Cl.[7] .............................................. C07C 39/24
(52) U.S. Cl. ....................... 568/779; 552/293; 552/309; 552/310
(58) Field of Search ...................... 568/779; 552/293, 552/309, 310

(56) References Cited

U.S. PATENT DOCUMENTS

| | | | |
|---|---|---|---|
| 1,934,656 A | 11/1933 | Britton et al. | |
| 3,213,114 A | 10/1965 | Braxton et al. | |
| 3,306,874 A | 2/1967 | Hay | |
| 3,658,852 A | 4/1972 | Schuster et al. | |
| 3,794,668 A | 2/1974 | Larkins, Jr. | |
| 3,796,732 A | 3/1974 | Brenner | |
| 3,859,317 A | 1/1975 | Hutchings | |
| 3,870,731 A | 3/1975 | Hutchings | |
| 3,933,681 A | 1/1976 | Hutchings et al. | |
| 3,987,068 A | 10/1976 | Reilly | |
| 4,208,339 A | 6/1980 | Costantini et al. | |
| 4,482,756 A | 11/1984 | Hsu et al. | |
| 4,519,948 A | 5/1985 | Hsu et al. | |
| 4,522,757 A | 6/1985 | Hsu et al. | |
| 5,177,258 A | 1/1993 | Becker et al. | |
| 5,932,753 A | 8/1999 | Onodera | |
| 6,410,798 B2 | 6/2002 | Maassen | |
| 6,693,221 B1 * | 2/2004 | Mills et al. | .................. 568/779 |

FOREIGN PATENT DOCUMENTS

EP    93540 A2    4/1983

OTHER PUBLICATIONS

Copending U.S. patent application Ser. No. 10/342,475, filed Jan. 16, 2003, By G. Soloveichik et al, entitled "Bromination of Hydroxyaromatic Compounds and Further Conversion to Dihydroxyaromatic Compounds".

Polymers of Carbonic Acid. 3. "Thermotropic Polycarbonates Derived From 4,4'—Dihydroxybiphenyl and Various Diphenols". Kricheldorf and Lubbers. Macromolecules 1990, 2656–2662.

\* cited by examiner

Primary Examiner—Michael L. Shippen
(74) Attorney, Agent, or Firm—Heslin Rothenberg Farley & Mesiti P.C.; Martha L. Boden, Esq.

(57) ABSTRACT

A method is described for the simultaneous preparation of p-bromophenols and p-benzoquinones, intermediates useful in the preparation of hydroquinones and 4,4'-dihydroxybiphenyls, respectively. Hydroquinones and 4,4'-dihydroxybiphenyls are useful monomers for the preparation of a variety of polymers. The method also comprises reducing the p-benzoquinone to its corresponding hydroquinone in the presence of the p-bromophenol. Limiting the amount of HBr present in the reaction mixture was shown to control the amount of benzoquinone produced. The method also allows for the recycling of many of the reagents used, thereby reducing the cost of producing each monomer.

22 Claims, No Drawings

METHOD FOR PREPARING HYDROQUINONES AND DIHYDROXYBIPHENYL COMPOUNDS FROM MIXTURES OF BROMOPHENOLS AND BENZOQUINONES

CROSS-REFERENCE TO RELATED APPLICATIONS

This Application is a continuation-in-part of Ser. No. 10/406,061 filed Apr. 4, 2003, entitled "METHOD OF PREPARING MIXTURES OF BROMOPHENOLS AND BENZOQUINONES", now U.S. Pat. No. 6,693,221 issued Feb. 17, 2004, which is hereby incorporated by reference herein in its entirety.

This Application is related to the following U.S. patent application/patent:

U.S. Ser. No. 10/342,475 pending, filed Jan. 16, 2003, entitled "BROMINATION OF HYDROXYAROMATIC COMPOUNDS AND FURTHER CONVERSION TO DIHYDROXYAROMATIC COMPOUNDS", which is hereby incorporated by reference herein in its entirety.

BACKGROUND OF THE INVENTION

This invention relates to a method of preparing in a single step, a mixture comprising a p-brominated phenol and a p-benzoquinone. More particularly the method relates to a method of preparing in a single step, a mixture of p-bromophenol and p-benzoquinone intermediates which may subsequently be converted in single step transformations to hydroquinones and dihydroxy aromatic compounds useful in the preparation of polycarbonate copolymers.

A variety of copolymers possessing useful and desirable properties comprise structural units derived from both hydroquinones and 4,4'dihydroxybiphenyls. Examples of include the polyether sulfone (CAS No. 90337-94-3) prepared from hydroquinone (HQ), 4,4'-dihydroxybiphenol (BP) and bis(4-chlorophenyl)sulfone; and the polyester (CAS No. 96892-06-7) derived from HQ, BP and a mixture of iso- and terephthalic acid. Additionally, polycarbonates comprising structural units derived from HQ, BP and another bisphenol comonomer (e.g. CAS No. 491588-47-7) show promise in a variety of materials applications.

Typically, the hydroquinone derivative and the 4,4'-dihydroxybiphenyl derivative used in the preparation of such polymers are prepared in independent manufacturing steps. Hydroquinone is typically prepared by air oxidation and fragmentation of 1,4-diisopropylbenzene, or by direct oxidation of phenol. Typically, 4,4'-dihydroxybiphenyl is obtained by oxidative coupling of 2,6-di-tert-butylphenol followed by acid mediated removal of the tert-butyl groups in the coupled product. Hydroquinones may be prepared as well by hydrolysis of a p-bromophenol as illustrated in U.S. Pat. No. 1,934,656. In addition, 4,4'-dihydroxybiphenyls may be prepared by reductive coupling of a p-bromophenol to the corresponding 4,4'-dihydroxybiphenyl as described in U.S. Pat. No. 5,177,258.

Commonly assigned, co-pending U.S. application Ser. No. 10/342,475 (filed Jan. 16, 2003) discloses an efficient means of preparing a p-bromophenol as a single intermediate which can be transformed by hydrolysis or reductive coupling into either a hydroquinone or a 4,4'-dihydroxybiphenyl. While this approach provides additional efficiencies based upon its use of a single intermediate p-bromophenol relative to known methods, improved methods continue to be sought, especially in light of the challenges presented by the rigorous conditions required for the hydrolytic transformation of the intermediate p-bromophenol to the corresponding hydroquinone.

The present invention is related to that described in co-pending U.S. application Ser. No. 10/342,475 (filed Jan. 16, 2003), but provides an alternate approach to the preparation of hydroquinones and 4,4'-dihydroxybiphenyls which eliminates the need for hydrolytic conversion of a p-bromophenol intermediate into the corresponding hydroquinone.

Furthermore, previous methods for the production of hydroquinone and 4,4'-biphenol have focused on the optimization of individual processes for each of the monomers. However, in order to reduce investment-related manufacturing costs at low production volume, it would be advantageous if the subsequent conversion of the benzoquinone could be conducted in the presence of the p-bromophenol intermediate, thus reducing the manufacturing cost of each of the desired products. Furthermore, it would be economical if the reagents used in the processes could be recycled to prepare additional intermediates. The present invention meets these needs.

BRIEF SUMMARY OF THE INVENTION

In one aspect, the present invention provides a method preparing a mixture of a p-bromophenol and a p-benzoquinone. The method comprises contacting in a reaction mixture a hydroxyaromatic compound with:

(a) hydrogen bromide;

(b) at least one source of copper selected from the group consisting of copper compounds, and elemental copper; and (c) oxygen gas;

The hydrogen bromide is present in an amount corresponding to less than 0.2 moles of hydrogen bromide per mole of the hydroxyaromatic compound, and the contacting takes place at a temperature ranging from about 20° C. to about 250° C.

In another aspect, the present invention relates to a method for the preparation of hydroquinones and 4,4'-dihydroxybiphenyls. The method comprises conversion of a mixture of a p-bromophenol and a pbenzoquinone into purified forms of the corresponding 4,4'-dihydroxybiphenyl derivative and the corresponding hydroquinone derivative.

In another aspect, the present invention provides a method for preparing a mixture of a p-bromophenol and a 1,4-hydroquinone derivative. The first step of the process comprises contacting in a reaction mixture the hydroxyaromatic compound with hydrogen bromide, oxygen gas, and a source of copper selected from the group consisting of copper compounds and elemental copper at a temperature ranging from about 20° C. to about 250° C., wherein hydrogen bromide is present in an amount corresponding to less than 0.2 moles of hydrogen bromide per mole of the hydroxyaromatic compound. The product mixture comprises a p-bromophenol, a 1,4-benzoquinone derivative, and the source of copper. In the second step, additional hydrogen bromide and water are added to the product mixture of the first step to produce an aqueous phase comprising the source of copper, unreacted hydrogen bromide, and water, and an organic phase comprising the p-bromophenol, and the 1,4-benzoquinone derivative. The aqueous phase is separated from the organic phase. The third step comprises contacting the separated organic phase with a metal catalyst and hydrogen gas to produce a resulting mixture comprising the p-bromophenol and the 1,4-hydroquinone derivative.

DETAILED DESCRIPTION OF THE INVENTION

The present invention may be understood more readily by reference to the following detailed description of preferred embodiments of the invention and the examples included herein. In this specification and in the claims which follow, reference will be made to a number of terms which shall be defined to have the following meanings.

The singular forms "a", "an" and "the" include plural referents unless the context clearly dictates otherwise.

"Optional" or "optionally" means that the subsequently described event or circumstance may or may not occur, and that the description includes instances where the event occurs and instances where it does not.

As used herein the term "polycarbonate" refers to polycarbonates incorporating structural units derived from one or more dihydroxy aromatic compounds and includes copolycarbonates and polyester carbonates.

As used herein, the term "melt polycarbonate" refers to a polycarbonate made by the transesterification of at least one diaryl carbonate with at least one dihydroxy aromatic compound.

"BPA" is herein defined as bisphenol A and is also known as 2,2-bis(4-hydroxyphenyl)propane, 4,4'-isopropylidenediphenol and p,p-BPA.

As used herein the terms "aryl" and "aromatic radical" refer to a radical having a valence of at least one and comprising at least one aromatic ring. Examples of aromatic radicals include phenyl, pyridyl, furanyl, thienyl, naphthyl, phenylene, and biphenyl. The term includes groups containing both aromatic and aliphatic components, for example a benzyl group, a phenethyl group or a naphthylmethyl group. The term also includes groups comprising both aromatic and cycloaliphatic groups for example 4-cyclopropylphenyl and 1,2,3,4-tetrahydronaphthalen-1-yl.

As used herein the terms "alkyl" and "aliphatic radical" refer to a radical having a valence of at least one and consisting of a linear or branched array of atoms which is not cyclic. The array may include heteroatoms such as nitrogen, sulfur and oxygen or may be composed exclusively of carbon and hydrogen. Examples of aliphatic radicals include methyl, methylene, ethyl, ethylene, hexyl, hexamethylene and the like.

As used herein the terms "cycloalkyl" and "cycloaliphatic radical" refer to a radical having a valance of at least one and comprising an array of atoms which is cyclic but which is not aromatic, and which does not further comprise an aromatic ring. The array may include heteroatoms such as nitrogen, sulfur and oxygen or may be composed exclusively of carbon and hydrogen. Examples of cycloaliphatic radicals include cyclopropyl, cyclopentyl cyclohexyl, 2-cyclohexylethy-1-yl, tetrahydrofuranyl and the like.

The present invention relates to a method of transforming a phenol 1 into a mixture of a p-bromophenol II and a p-benzoquinone III

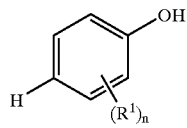

I

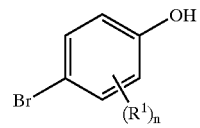

II

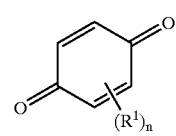

III wherein, in each of structures I, II and III, $R^1$ is independently at each occurrence a $C_1$–$C_{20}$ alkyl group, $C_4$–$C_{20}$ cycloalkyl group, or a $C_4$–$C_{20}$ aryl group, and n is an integer from 0 to 4. The product mixture may also comprise a corresponding o-bromophenol by-product, as well as more highly brominated by-products.

As used herein, "ortho-" refers to the 2- or 6- position on the aryl ring relative to the carbon in the 1-position attached to the hydroxy group. Likewise, "meta-" refers to the 3- or 5- position, and "para-" refers to the 4-position. Furthermore, "o-" refers to ortho-; "m-" refers to meta-; and "p-" refers to para-.

The present invention also relates to a method for preparing 4,4'-dihydroxybiphenyl compounds and 1,4-hydroquinone derivatives from the mixture comprising a p-bromophenol II and a p-benzoquinone derivative TI. An unexpected advantage of the present invention is that conversion of the p-benzoquinone derivative to the desired 1,4-hydroquinone can be conducted in the presence of the p-bromophenol II, as well as any other brominated by-products, in the same piece of equipment, without degradation of the bromophenols. Furthermore, the 1,4-hydroquinone product, as well as the p-bromophenol, may then each be separated from the resulting mixture. The isolated p-bromophenol may be reductively coupled to form the desired dihydroxybiphenyl compound. In addition, many of the reagents used in the process, such as the copper catalyst, unreacted hydroxyaromatic compound, and unreacted HBr may also be recycled into a subsequent process.

Thus, in one embodiment of the present invention a product mixture comprising p-bromophenol II and benzoquinone III is subjected to a separation step to provide p-bromophenol II and p-benzoquinone III in purified form. A significant advantage of the method of the present invention over known methods is that it provides the intermediate p-benzoquinone III which may be transformed under very mildly reducing conditions to hydroquinone derivative IV

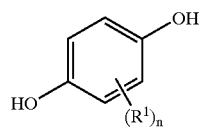

IV wherein $R^1$ and n are defined as in structures I–III. Purified p-bromophenol II may be transformed via reductive coupling into 4,4'-dihydroxybiphenyl derivative V

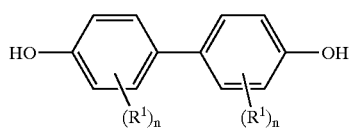

wherein $R^1$ and n are defined as in structures I–II.

Physical methods which may be used to separate a mixture comprising p-bromophenol II and p-benzoquinone III into purified forms of H and III include fractionation by distillation, vacuum distillation, steam distillation, sublimation, crystallization, zone refining and like techniques, or a combination of one or more of such techniques. Typically, fractional distillation and crystallization are preferred. In one embodiment, the mixture of p-bromophenol II and p-benzoquinone III prepared by the method of the present invention is separated by fractional distillation and recrystallization into purified forms of p-bromophenol II and p-benzoquinone III having purities in excess of 90 percent, preferably in excess of 95 percent, and still more preferably in excess of 98 percent. In one embodiment a mixture comprising 4-bromophenol (CAS No. 106-41-2) and 1,4-benzoquinone (CAS No. 105-51-4) prepared from phenol using the method of the present invention, is separated by fractional distillation and recrystallization of the resultant distillation fractions to provide purified 4-bromophenol and 1,4-benzoquinone having purities in excess of 90 percent.

In another embodiment, the mixture comprising p-bromophenol II and p-benzoquinone III is subjected to mild reduction of the p-benzoquinone component to hydroquinone IV prior to separation from p-bromophenol II and other by-products. Reduction methods for transforming benzoquinones into the corresponding hydroquinones are well known in the art and include catalytic reduction using hydrogen and a noble metal catalyst, for example, reduction with hydrogen gas using palladium on carbon as the catalyst at ambient temperature and pressure. Other reduction catalysts include, but are not limited to, Raney nickel, palladium on alumina, palladium on barium carbonate, palladium on barium sulfate, palladium on strontium carbonate, palladium on calcium carbonate, and the like.

The method of the present invention is carried out by first contacting a hydroxyaromatic compound with hydrogen bromide (HBr), a source of copper, optionally an organic solvent, and oxygen gas at a temperature in a range between about 20° C. and about 250° C., preferably between about 30° C. and about 150° C., and even more preferably between about 40° C. and about 100° C. The amount of hydrogen bromide plays a key role in producing high levels of benzoquinone product. The amount of hydrogen bromide should range from about 0.01 to about 0.2 moles, preferably range from about 0.02 to about 0.15 moles, and still more preferably range from about 0.04 to about 0.1 moles of hydrogen bromide per mole of the hydroxyaromatic compound.

Hydrogen bromide may be employed in any form; examples include gaseous HBr, aqueous HBr (hydrobromic acid), and HBr in solution in a polar solvent, such as acetic acid, for example. Hydrobromic acid may be employed at any concentration, including the commercially available 48% aqueous solution (i.e. a mixture of hydrogen bromide and water comprising about 48 percent by weight HBr and about 52 percent by weight water).

Typically, the hydroxyaromatic compound is a phenol bearing no substituent in the position para to the phenolic OH group, for example structure I

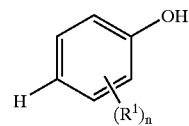

wherein $R^1$ is independently at each occurrence a $C_1$–$C_{20}$ alkyl group, $C_4$–$C_{20}$ cycloalkyl group, or a $C_4$–$C_{20}$ aryl group, and n is an integer from 0 to 4.

Examples of phenols having structure 1 include phenol, o-cresol, m-cresol; 2,6-xylenol; 2,5-xylenol; 2,3,5-xylenol; 2,3,6-xylenol; 2-ethylphenol, 2-propylphenol, 2-tert-butylphenol, 2-phenylphenol, and the like. Typically, phenol and o-cresol are preferred.

The method of the present invention requires only catalytic amounts of copper but typically involves the use of a substantial stoichiometric excess of oxygen. Typically, the hydroxyaromatic compound is reacted in the presence of aqueous HBr, a copper species, an organic solvent (optional), and oxygen in a reaction vessel equipped for intimate mixing of the reactants and operation at pressures higher than atmospheric pressure. In one embodiment, the reactants other than oxygen are first charged to a batch reaction vessel and stirring is begun. Subsequently a stoichiometric excess of oxygen gas is introduced into the reaction vessel to provide a partial pressure of oxygen over the reaction mixture ranging from about 1 atm to about 140 atm, preferably from about 3 atm to about 100 atm, and still more preferably from about 7 atm to about 34 atm. In an alternate embodiment, the reactants are introduced into a flow reactor, for example a continuous stirred tank reactor, agitated and exposed to oxygen under conditions corresponding to partial pressure of oxygen over the reaction mixture ranging from about 1 atm to about 140 atm, preferably from about 3 atm to about 100 atm, and still more preferably from about 7 atm to about 34 atm. In almost any embodiment of the invention, the oxygen gas may be used advantageously in the form of pure oxygen, air, an oxygen-enriched air mixture, a synthetic mixture of oxygen and one or more other gases (for example, a synthetic mixture of oxygen and nitrogen), or any other convenient source of oxygen which may be used as the stoichiometric oxidant. Reaction vessels for use according to the method of the invention include stirred tank reactors, continuous stirred tank reactors and the like.

As mentioned, the source of copper employed is present in a catalytic amount and can be any copper source capable of producing copper ions under the reaction conditions. Thus, even elemental copper or a mixture of copper compounds may be used according to the method of the invention. As used herein, the term "copper catalyst" and "source of copper" have the same meaning and are used interchangeably. It has been found most convenient, however, to employ a catalytic amount of copper in the form of a single soluble copper compound, such as a copper halide. The initial oxidation state of the copper compound employed does not appear to be critical, so that cuprous halides and cupric halides may be employed with reasonable interchangeability. Typically, the source of copper will be selected from the group consisting of cuprous chloride, cuprous bromide, cuprous iodide, cupric chloride, cupric bromide, and cupric iodide. Owing to their greater overall stability cupric halides are typically preferred.

Typically, the source of copper employed is used in an amount sufficient to provide a concentration of copper ion in the reaction mixture in an amount ranging from about 0.001 to about 0.200 moles, preferably from about 0.01 to about 0.1 moles, and still more preferably from about 0.03 to about 0.07 moles of copper ion per mole of hydroxyaromatic compound.

The method of the present invention may be advantageously carried out in the presence of an organic solvent which may be a pure solvent, or a mixture of solvents. Typically it is preferred that the organic solvent comprise an organic nitrile solvent, for example acetonitrile. Organic nitrile solvents are illustrated by acetonitrile, propionitrile, butyronitrile, isopropyinitrile, benzonitrile, and mixtures thereof. In some embodiments an organic nitrile solvent is used as a mixture with one or more solvents selected from the group consisting of aliphatic ethers, aromatic ethers, aliphatic alcohols, aromatic alcohols, ketones, halogenated alkanes, halogenated aromatics, amides, aliphatic hydrocarbons, and aromatic hydrocarbons. Typically, the organic solvent is present in an amount ranging from about 0.01 to about 1.0 liters, preferably from about 0.01 to about 0.5 liters, and sill more preferably from about 0.1 to about 0.4 liters of organic solvent per mole of hydroxyaromatic compound employed.

In addition, it is often beneficial to add water to the reaction mixture. In this embodiment, water is added to the reaction mixture in an amount corresponding to about 0.4 moles to about 5 moles, preferably from about 1 mole to about 5 moles, and still more preferably from about 1 mole to about 3 moles of water per mole of hydroxyaromatic compound.

In one embodiment, phenol is reacted under the conditions of the present invention to provide a mixture of 4-bromophenol with 1,4-benzoquinone. This embodiment of the present invention is practiced by contacting in a reaction mixture at a temperature in a range from about 20° C. to about 150° C., phenol with hydrogen bromide, at least one source of copper selected from the group consisting of cupric bromide or cuprous bromide, acetonitrile (optional); and oxygen gas. The hydrogen bromide is present in an amount corresponding to less than 0.2 moles of hydrogen bromide per mole of phenol. The source of copper is present in an amount ranging from about 0.01 to about 0.20 moles of copper per mole of phenol. The acetonitrile, when present, is present in an amount ranging from about 0.01 to about 1.0 liters of acetonitrile per mole of phenol, and the "contacting" is carried out under a partial pressure of oxygen ranging from about 1 to about 140 atm. The product obtained is a mixture comprising 4-bromophenol and 1,4-benzoquinone.

In an alternate embodiment, o-cresol is reacted under the conditions of the present invention to provide a mixture of 4-bromo-2-methylphenol with 2-methyl-1,4-benzoquinone. This embodiment of the present invention is practiced by contacting in a reaction mixture at a temperature ranging from about 20° C. to about 150° C., o-cresol with: hydrogen bromide, at least one source of copper selected from the group consisting of cupric bromide or cuprous bromide, acetonitrile (optional), and oxygen gas. The hydrogen bromide is present in an amount corresponding to less than 0.2 moles of hydrogen bromide per mole of o-cresol. The source of copper is present in an amount ranging from about 0.01 to about 0.20 moles of copper per mole of o-cresol. The acetonitrile, when present, is present in an amount ranging from about 0.01 to about 1.0 liters of acetonitrile per mole of phenol, and the "contacting" is carried out under a partial pressure of oxygen ranging from about 1 to about 140 atm. The product obtained is a mixture comprising 4-bromo-2-methylphenol and 2-methyl-1,4-benzoquinone.

Typically, the percentage of a phenolic compound having structure 1, converted to p-bromophenol II and p-benzoquinone III is at least 20 percent, preferably at least 25 percent, and still more preferably at least 30 percent. Typically, the selectivity for the production of p-bromophenol II is in a range from about 20 to about 80 percent. This means that for every mole of phenolic compound 1 converted to products, between about 0.2 and about 0.8 moles of a p-bromophenol II is produced. Correspondingly, the selectivity for the production of p-benzoquinone III is in a range from about 80 to about 20 percent. Other products, for example 2-bromophenols, or more highly brominated products, may be formed during the reaction such that the sum of the selectivities for the p-bromophenol II and the p-benzoquinone III need not be 100%.

As previously mentioned, the method of the present invention described above produces a product mixture comprising a p-bromophenol II and a 1,4-benzoquinone III derivative III. The source of copper is also included in the product mixture. However, in another aspect of the invention, the 1,4-benzoquinone derivative III is subsequently reduced to the corresponding 1,4-hydroquinone derivative IV in the presence of the p-bromophenol product 11.

In this embodiment, prior to reduction of the 1,4-benzoquinone derivative III, the source of copper may easily be removed from the product mixture, thereby eliminating the need to isolate the benzoquinone from the mixture. Beneficially, the copper catalyst may then be reused in a subsequent oxybromination reaction of hydroxyaromatic compound 1, such as that previously described. Removal of the copper catalyst from the product mixture may be facilitated by adding additional HBr and water to create two phases. Typically, aqueous HBr (48 wt. %) is added, as well as additional water. In this case, the total amount of HBr (48 wt. %) and water added to the product mixture generally does not exceed 20% (up to about 20%) of the weight of the initial copper-containing reaction mixture. In addition, the ratio of 48% HBr to water that is added typically ranges from about 1:1 (24% HBr) to about 1:9 (4.8% HBr). However, as will be obvious to one of ordinary skill in the chemical arts, the amounts of HBr and water added to the product mixture may be adjusted accordingly when other forms of HBr are employed.

The copper catalyst, unused HBr and water reside predominantly in the aqueous phase, and the oxybromination products, i.e. p-bromophenol II, as well as any corresponding o-bromophenol by-products, and the 1,4-benzoquinone derivative, reside predominantly in the organic phase. The two phases may then be separated using conventional techniques, such as by decantation, or by using a separatory funnel, a separation tank, or a continuous separation colurnn, for example, and the organic phase is removed. The aqueous phase comprising the source of copper and unreacted hydrogen bromide may then be recycled, all or in part, into a subsequent oxybromination reaction, such as previously described. Often, to avoid the accumulation of water, a portion of the water may be removed from the aqueous phase prior to recycling. This can be done by commonly known techniques, such as by vacuum distillation.

Often an organic solvent, such as one or more of the organic nitriles previously listed, may be present with the reactants in the initial oxybromination reaction, as well as in the product mixture. In this embodiment, prior to the addition of HBr and water, at least a portion of the organic solvent may optionally be removed from the product mixture, typically by vacuum distillation, in order to obtain phase separation. However, to facilitate evaporation and removal from the product mixture, the organic solvent should have a boiling point lower than that of water, such as acetonitrile, which has a boiling point of 81–82° C.

Advantageously, the 1,4-benzoquinone III included in the organic phase can then be reduced to the corresponding 1,4-hydroquinone IV without separating the 1,4-benzoquinone derivative III from the p-bromophenol II or any by-products. The reduction may be conducted using conventional techniques such as by using hydrogen gas as the reducing agent, and a metal catalyst at ambient temperature and pressure. As used herein, the term "metal catalyst" means a reduction catalyst, such as palladium or nickel. Examples include, but are not limited to, Raney nickel, palladium on carbon, palladium on alumina, palladium on barium carbonate, palladium on barium sulfate, palladium on strontium carbonate, palladium on calcium carbonate, and other supported palladium catalysts. Typically, the metal catalyst will be heterogeneous, but need not be. Excess hydrogen gas is introduced into the reaction vessel to provide a partial pressure of hydrogen over the reaction mixture ranging from about 1 atm to about 140 atm, preferably from 2 atm to about 100 atm, and still more preferably from about 3 atm to about 34 atm. After this step, a mixture of the p-bromophenol II and the 1,4-hydroquinone derivative IV remains in the reaction vessel. The reduction catalyst may then be removed, typically by filtration, and may be reused in a subsequent reduction of benzoquinone, if desired.

In one embodiment, when the hydroxayaromatic compound I is phenol, the desired hydroquinone derivative IV is 1,4-hydroquinone. In another embodiment, the hydroxayaromatic compound 1 is o-cresol, and the hydroquinone derivative IV is 2-methyl-1,4-hydroquinone.

Optionally, prior to the reduction of the benzoquinone derivative III, the organic phase may be washed with water at least one time, but preferably up to three times, to remove any traces of the copper catalyst, as well as any traces of unreacted HBr. The wash water is then removed and may be combined with the aqueous phase for recycling to another oxybromination reaction. Again, much of the water is typically removed prior to recycling.

After the reduction of benzoquinone III is complete, the 1,4-hydroquinone derivative IV and the p-bromophenol II may be separated from the resulting mixture. Separation of these compounds into their purified forms may be effected by art-recognized methods, such as those previously listed, including fractionation by distillation, vacuum distillation, steam distillation, sublimation, crystallization, zone refining and like techniques, or a combination of one or more of such techniques. Again, fractional distillation is preferred, because, for example, in one embodiment, wherein a mixture of 4 bromophenol and 1,4-hydroquinone is produced from phenol, there is a difference of more than 55° C. between the boiling points of 4 bromophenot (238° C.) and 1,4-hydroquinone (295° C.). Purities in excess of 90 percent are obtained, but are preferably in excess of 95 percent, and still more preferably in excess of 98 percent. One to three distillations are generally sufficient. Distillation may be conducted under reduced pressure to minimize thermal decomposition.

After separation, the purified 1,4-hydroquinone derivative IV obtained from the conversion of the hydroxyaromatic compound, may then be used in the synthesis of various copolymers, as previously described. The p-bromophenol II fraction may undergo reductive coupling to form a 4,4'-dihydroxybiphenyl compound having structure V. Reductive coupling reactions are fully described, for example, in U.S. Pat. No. 5,177,258.

In one embodiment, wherein phenol is the hydroxyaromatic compound 1 and 4-bromophenol is the p-bromophenol II, the 4,4'-dihydroxybiphenyl derivative V formed is 4,4'-dihydroxybiphenyl, i.e., biphenol. In another embodiment, when o-cresol is the starting compound, the p-bromophenol II is 4-bromo-2-methylphenol, and the 4,4'-dihydroxybiphenyl derivative V is 2,2'-dimethyl-4,4'-dihydroxybiphenyl. The 4,4'-dihydroxybiphenyl derivative V may then be used in the synthesis of copolymers, as previously described.

EXAMPLES

The following examples are set forth to provide those of ordinary skill in the art with a detailed description of how the methods claimed herein are carried out and evaluated, and are not intended to limit the scope of what the inventors regard as their invention. Unless indicated otherwise, parts are by weight, temperature is in ° C. The reagents, reactants, and catalysts used in the reactions described herein are readily available materials.

EXAMPLE 1

An amber 3 dram vial was charged with phenol (1.33 mL, 15.00 mmol), 48 percent hydrobromic acid (0.118 mL, 1.0 mmol of hydrogen bromide), cupric bromide (340 milligrams, 1.5 mmol) and acetonitrile (3.18 mL). The vial was loaded into an aluminum block, placed inside an autoclave and pressurized with air (1000 psi). Upon heating at 65° C. for 2 hours the autoclave was allowed to cool and the product mixture was analyzed by gas chromatography. The product mixture was found to contain 4-bromophenol (6.50% by weight), 2-bomophenol (2.00% by weight) and p-benzoquinone (6.75% by weight). These product concentrations corresponded to 54 percent overall conversion of phenol to products with a selectivity for 4-bromophenol of 23 percent and a selectivity for p-benzoquinone of 37 percent.

EXAMPLE 2

An amber 3 dram vial was charged with phenol (1.33 mL, 15.00 mmol), 48 percent hydrobromic acid (0.118 mL, 1.0 mmol of hydrogen bromide), cupric bromide (340 milligrams, 1.5 mmol) and acetonitrile (3.18 mL). The vial was loaded into an aluminum block, placed inside an autoclave and pressurized with air (500 psi). Upon heating at 65° C. for 2 hours the autoclave was allowed to cool and the product mixture was analyzed by gas chromatography. The product mixture was found to contain 4-bromophenol (6.0% by weight), 2-bromophenol (2.30% by weight) and p-benzoquinone (3.25% by weight). These product concentrations corresponded to 35 percent overall conversion of phenol to products with a selectivity for 4-bromophenol of 30 percent and a selectivity for p-benzoquinone of 26 percent.

EXAMPLE 3

An amber 3 dram vial was charged with phenol (1.25 mL, 14.00 mmol), 48 percent hydrobromic acid (0.118 mL, 1.00 mmol of hydrogen bromide), cupric bromide (156 milligrams, 0.70 mmol), water (0.45 mL, 25.00 mmol) and acetonitrile (3.18 mL). The vial was loaded into an aluminum block, placed inside an autoclave and pressurized with air (68 atm). Upon heating at 65° C. for 2 hours the autoclave was allowed to cool and the product mixture was analyzed by gas chromatography. The product mixture was found to contain 4-bromophenol (3.96% by weight), 2-bomophenol (1.25% by weight) and p-benzoquinone (5.17% by weight). These product concentrations corresponded to 39 percent overall conversion of phenol to products with a selectivity for 4-bromophenol of 20 percent and a selectivity for p-benzoquinone of 41 percent.

EXAMPLE 4

An amber 3 dram vial was charged with o-cresol (1.47 mL, 14.00 mmol), 48 percent hydrobromic acid (0.118 mL, 1.0 mmol of hydrogen bromide), cupric bromide (156 milligrams, 0.7 mmol), water (0.45 mL, 25 mmol) and acetonitrile (2.91 mL). The vial was loaded into an aluminum block, placed inside an autoclave and pressurized with air (68 atm). Upon heating at 65° C. for 2 hours the autoclave was allowed to cool and the product mixture was analyzed by gas chromatography. The product mixture was found to contain 4-bromo-2-methylphenol (5.5% by weight), methyl-1,4-benzoquinone (6.40% by weight), and 6-bromo-2-methylphenol (0.6% by weight). These product concentrations corresponded to 45 percent overall conversion of o-cresol to products with a selectivity for 4-bromo-2-methylphenol of 22 percent and a selectivity for methyl-p-benzoquinone of 40 percent.

EXAMPLE 5

An amber 3 dram vial was charged with m-cresol (1.46 mL, 14.00 mmol), 48 percent hydrobromic acid (0.118 mL, 1.0 mmol of hydrogen bromide), cupric bromide (156 milligrams, 0.7 nimol), water (0.45 mL, 25 mmol) and acetonitrile (2.92 mL). The vial was loaded into an aluminum block, placed inside an autoclave and pressurized with air (68 atm). Upon heating at 65° C. for 2 hours the autoclave was allowed to cool and the product mixture was analyzed by gas chromatography. The product mixture was found to contain 4-bromo-3-methylphenol (6.2% by weight), methyl-p-benzoquinone (15.84% by weight). These product concentrations corresponded to 67 percent overall conversion of m-cresol to products with a selectivity for 4-bromo-3-methylphenol of 17 percent and a selectivity for methyl-p-benzoquinone of 65 percent.

COMPARATIVE EXAMPLE 1

To a 3-dram vial were charged 1.37 ml (15.56 mmol) of phenol, 0.112 g (0.5 mmol) of cupric bromide, 1.39 ml (12.50 mmol) of 48% hydrobromic acid and 2.20 ml of acetonitrile. The vial was sealed with a cap containing a hole to allow for air flow during the reaction and placed in an aluminum block. The block was placed in a 450-ml autoclave reactor, pressurized to 34.0 atm with air and heated at 65° C. for 1 hour. It was then cooled to room temperature and depressurized. The resulting mixture was analyzed by vapor phase chromatographic analysis and shown to contain 7.39% phenol, 28.63% 4-bromophenol, 5.59% 2-bromophenol and 0.68% 2,4-dibromophenol, corresponding to 72% phenol conversion, with 82% 4-bromophenol selectivity and a total monobromophenol selectivity of 98%.

COMPARATIVE EXAMPLE 2

To a 3-dram vial were charged 1.59 ml (15.39 mmol) of o-cresol, 0.112 g (0.5 nmmol) of cupric bromide, 1.48 ml (12.47 mmol) of 48% hydrobromic acid and 1.92 ml of acetonitrile. The vial was sealed and located as in Example 1, pressurized to 34.0 atm with air and heated at 65° C. for 1 hour. It was then cooled to room temperature and depressurized. The resulting mixture was analyzed by vapor phase chromatographic analysis and shown to contain 13.23% o-cresol, 27.74% 4-bromo-2-methylphenol and 0.93% 6-bromo-2-methylphenol, corresponding to 56% o-cresol conversion, with 96% 4-bromo-2-methylphenol selectivity and a total monobromophenol selectivity of 99%.

COMPARATIVE EXAMPLE 3

To a 3-dram vial were charged 1.37 ml (15.56 umnol) of phenol, 0.112 g (0.5 mmol) of cupric bromide, 1.30 ml (6.85 mmol) of a 30% solution of hydrogen bromide in acetic acid and 2.31 ml of acetonitrile. The vial was sealed and located as in Example 1, pressurized to 34.0 atm with air and heated at 65° C. for 1 hour. It was then cooled to room temperature and depressurized. The resulting mixture was analyzed by vapor phase chromatographic analysis and shown to contain 14.12% phenol, 19.15% 4-bromophenol and 1.15% 2-bromophenol, corresponding to 44% phenol conversion, with 96% 4-bromophenol selectivity and a total monobromophenol selectivity of 100%.

Results from Example 1 and Comparative Examples 1–3 are gathered in Table 1 and illustrate the surprising effect of acid concentration on the level of benzoquinone produced.

TABLE 1

| Example | ArOH[a] | [HBr][b] | % Conversion | "4-bromo" selectivity | benzo-quinone selectivity |
|---|---|---|---|---|---|
| Example 1 | phenol | 0.06 | 54% | 23% | 37% |
| Example 2 | phenol | 0.06 | 35% | 30% | 26% |
| Example 3* | phenol | 0.07 | 39% | 20% | 41% |
| Example 4 | o-cresol | 0.07 | 45% | 22% | 40% |
| Example 5* | m-cresol | 0.07 | 67% | 17% | 65% |
| CE-1[c] | phenol | 0.8 | 72% | 96% | 0% |
| CE-2[c] | o-cresol | 0.8 | 56% | 96% | 0% |
| CE-3[c] | phenol | 0.4 | 44% | 96% | 0% |

[a]ArOH = hydroxyaromatic compound
[b]moles HBr per mole ArOH employed
[c]Comparative Example
*Water added

EXAMPLE 6

The procedure of Example 1 was followed. A fraction of the acetonitrile is then evaporated from the product mixture at 60° C. under vacuum, such that it represents a mass fraction of less than 20% of the resulting remaining mixture. To the resulting mixture is added 2 g of HBr (48 wt. % in water) and 3 g water, whereupon, a two-phase mixture is formed at 50° C. The phases are separated and analyzed. The aqueous phase contains>98% of the Cu fed into the reactor originally. The organic phase contains most of the 2-bromophenol, 4-bromophenol, and 1,4-benzoquinone (>75% of each component). The organic phase is then washed with water, and the water wash is combined with the aqueous phase already collected. The combined aqueous phase is then partially evaporated to remove a fraction of the water. The remaining mixture, comprising water, HBr, and a Cu compound, can then be used as the source of Cu catalyst and HBr in a subsequent oxidationibromination reaction. After the water wash has been removed, the organic phase is then sent to a reduction reaction: Pd/C catalyst is added to the organic phase to form a slurry, and the mixture is then subjected to $H_2$ pressure (6.8 atrn) for 3 hours. The resulting mixture is filtered to separate the Pd/C catalyst, and the liquid stream is analyzed. 1,4-Benzoquinone is converted to 1,4-hydroquinone (>95%), while the bromophenols are relatively unaffected (>95% remaining from the mixture fed to the reduction reaction).

The invention has been described in detail with particular reference to preferred embodiments thereof, but it will be understood by those skilled in the art that variations and modifications can be effected within the spirit and scope of the invention.

What is claimed is:

1. A method of preparing a mixture of a p-bromophenol and a p-benzoquinone, said method comprising contacting in a reaction mixture a hydroxyaromatic compound with:
    (a) hydrogen bromide;
    (b) at least one source of copper selected from the group consisting of copper compounds, and elemental copper; and
    (c) oxygen gas,
   said hydrogen bromide being present in an amount corresponding to less than 0.2 moles of hydrogen bromide per mole of said hydroxyaromatic compound, said contacting taking place at a temperature ranging from about 20° C. to about 250° C. and carried out under pressure, said pressure ranging from about 1 atm to about 140 atm.

2. The method according to claim 1 wherein said oxygen gas is present as a mixture with nitrogen gas or as air or as an oxygen-enriched air mixture.

3. A method of preparing a mixture of a p-bromophenol and a p-benzoquinone, said method comprising contacting in a reaction mixture a hydroxyaromatic compound with:
    (a) hydrogen bromide;
    (b) at least one source of copper selected from the group, consisting of copper compounds, and elemental copper;
    (c) oxygen gas; and
    (d) water in an amount ranging from about 0.4 moles to about 5 moles of water per mole of said hydroxyaromatic compound;
   said hydrogen bromide being present in an amount corresponding to less than 0.2 moles of hydrogen bromide per mole of said hydroxyaromatic compound, said contacting taking place at a temperature ranging from about 20° C. to about 250° C.

4. A method of preparing a mixture of a p-bromophenol and a p-benzoquinone, said method comprising contacting in a reaction mixture a hydroxyaromatic compound with:
    (a) aqueous hydrogen bromide;
    (b) at least one source of copper selected from the group consisting of copper compounds, and elemental copper; and
    (c) oxygen gas;
   said aqueous hydrogen bromide being present in an amount corresponding to less than 0.2 moles of hydrogen bromide per mole of said hydroxyaromatic compound, said contacting taking place at a temperature ranging from about 20° C. to about 250° C.

5. A method for the preparation of 4-bromophenol as a mixture with 1,4-benzoquinone, said method comprising contacting in a reaction mixture at a temperature ranging from about 20° C. to about 150° C., phenol with:
    (a) aqueous hydrogen bromide;
    (b) at least one source of copper selected from the group consisting of cupric bromide or cuprous bromide;
    (c) acetonitrile; and
    (d) oxygen gas;
said aqueous hydrogen bromide being present in an amount corresponding to less than 0.2 moles of hydrogen bromide per mole of phenol, said source of copper being present in an amount ranging from about 0.01 to about 0.20 moles of copper per mole of phenol, said acetonitrile being present in an amount ranging from about 0.01 to about 1.0 liters of acetonitrile per mole of phenol, said contacting being carried out under a partial pressure of oxygen ranging from about 1 to about 140 atm.

6. The method according to claim 5 wherein said phenol is converted to said 4-bromophenol and said 1,4-benzoquinone to the extent of at least 20 percent.

7. The method according to claim 5 further comprising a separation step, said separation step comprising transforming said mixture comprising said 4-bromophenol and said 1,4-benzoquinone into purified 4-bromophenol having a purity of at least 90 percent, and purified 1,4-benzoquinone having a purity of at least 90 percent.

8. A method for the preparation of 4-bromo-2-methylphenol as a mixture with 2-methyl-1,4-benzoquinone, said method comprising contacting in a reaction mixture at a temperature ranging from about 20° C. to about 150° C., o-cresol with:
    (a) aqueous hydrogen bromide;
    (b) at least one source of copper selected from the group consisting of cupric bromide or cuprous bromide;
    (c) acetonitrile; and
    (d) oxygen gas;
said aqueous hydrogen bromide being present in an amount corresponding to less than 0.2 moles of hydrogen bromide per mole of o-cresol, said source of copper being present in an amount ranging from about 0.01 to about 0.20 moles of copper per mole of o-cresol, said acetonitrile being present in an amount ranging from about 0.01 to about 1.0 liters of acetonitrile per mole of o-cresol, and said contacting being carried out under a partial pressure of oxygen ranging from about 1 to about 140 atm.

9. A method for preparing a mixture of a p-bromophenol and a 1,4-hydroquinone derivative, said method comprising:
    (a) contacting in a reaction mixture a hydroxyaromatic compound with hydrogen bromide, oxygen gas, and at least one source of copper selected from the group consisting of copper compounds and elemental copper at a temperature ranging from about 20° C. to about 250° C., wherein said hydrogen bromide is present in an amount corresponding to less than 0.2 moles of hydrogen bromide per mole of said hydroxyaromatic compound, to produce a product mixture comprising said p-bromophenol, a 1,4-benzoquinone derivative, and said copper catalyst;
    (b) adding additional hydrogen bromide and water to said product mixture of step (a) to produce an aqueous phase comprising said copper catalyst, unreacted hydrogen bromide, and water, and an organic phase comprising said p-bromophenol and said 1,4-benzoquinone derivative, followed by the step of separating said aqueous phase from said organic phase; and
    (c) contacting said separated organic phase with a metal catalyst and hydrogen gas to produce a resulting mixture comprising said p-bromophenol and said 1,4-hydroquinone derivative.

10. The method according to claim 9, wherein said hydroxyaromatic compound has structure I

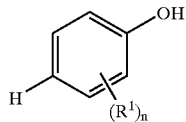

wherein $R^1$ is independently at each occurrence a $C_1-C_{20}$ alkyl group, $C_4-C_{20}$ cycloalkyl group, or a $C_4-C_{20}$ aryl group, and n is an integer from 0 to 4.

11. The method according to claim 10 wherein said hydroxyaromatic compound is phenol, and wherein said p-bromophenol is 4-bromophenol, and said 1,4-hydroquinone derivative is 1,4-hydroquinone.

12. The method according to claim 10 wherein said hydroxyaromatic compound is o-cresol, and wherein said p-bromophenol is 4-bromo-2-methylphenol, and said 1,4-hydroquinone derivative is 2-methyl-1,4-hydroquinone.

13. The method according to claim 9 wherein said at least one source of copper is present in an amount sufficient to provide copper ion to the reaction mixture in an amount ranging from about 0.001 to about 0.200 moles of copper ion per mole of hydroxyaromatic compound.

14. The method according to claim 9 wherein said copper compounds are selected from the group consisting of cuprous chloride, cuprous bromide, cuprous iodide, cupric chloride, cupric bromide, and cupric iodide.

15. The method according to claim 9 wherein said contacting in step (a) is carried out under pressure ranging from about 1 atm to about 140 atm.

16. The method according to claim 9 wherein said reaction mixture and said product mixture further comprise an organic solvent selected from the group consisting of acetonitrile, propionitrile, butyronitrile, isopropyinitrile, benzonitrile, and mixtures thereof, and wherein prior to step (b), at least a portion of said organic solvent is optionally removed from said product mixture.

17. The method according to claim 9 wherein said reaction mixture further comprises water in an amount corresponding to about 0.4 moles to about 5 moles of water per mole of said hydroxyaromatic compound.

18. The method of claim 9 wherein said hydrogen bromide is aqueous hydrogen bromide.

19. The method according to claim 9 wherein said metal catalyst comprises palladium or nickel.

20. The method according to claim 9 further comprising the step of recycling at least a portion of said aqueous phase comprising said copper catalyst and unreacted hydrogen bromide to a further method for preparing a mixture of a p-bromophenol and a 1,4-hydroquinone derivative, wherein a portion of water has optionally been removed from said aqueous phase prior to recycling.

21. The method according to claim 9 further comprising prior to step (c) the steps of:

(i) washing said separated organic phase with water at least one time to remove any traces of unreacted hydrogen bromide and any traces of said copper catalyst;

(ii) removing said wash water from said separated organic phase;

(iii) combining said wash water with said aqueous phase comprising said copper catalyst and unreacted hydrogen bromide, and optionally removing a portion of water from said combined aqueous phase and wash water; and (iv) recycling said combined aqueous phase and wash water, wherein a portion of water has optionally been removed, to a further method for preparing a mixture of a p-bromophenol and a 1,4-hydroquinone derivative.

22. The method according to claim 9 further comprising a separation step, said separation step comprising transforming said mixture comprising said p-bromophenol and said 1,4-hydroquinone derivative into a purified p-bromophenol having a purity of at least 90 percent, and a purified 1,4-hydroquinone derivative having a purity of at least 90 percent.

* * * * *